United States Patent [19]

Kozlowski

[11] 4,046,806
[45] Sept. 6, 1977

[54] METHOD OF PREPARING A DISALT OF 3,3-SULFONYLBIS (6-HYDROXYBENZENE SULFONIC ACID)

[75] Inventor: John H. Kozlowski, Vancouver, Wash.

[73] Assignee: Crown Zellerbach Corporation, San Francisco, Calif.

[21] Appl. No.: 612,598

[22] Filed: Sept. 12, 1975

[51] Int. Cl.$^2$ ............................................. C07C 143/42
[52] U.S. Cl. ........................... 260/512 C; 106/15 FP; 210/59; 260/DIG. 24
[58] Field of Search .................................. 260/512 C

[56] References Cited

U.S. PATENT DOCUMENTS

| | | | |
|---|---|---|---|
| 2,171,806 | 9/1939 | Russell et al. | 260/49 |
| 3,663,509 | 5/1972 | Bonnard et al. | 260/512 C |

OTHER PUBLICATIONS

Zehenter et al., J. Prakt. Chem., 117, 233 (1927).
Zehenter et al., Chem. Abstract, 22, 949 (1928).

*Primary Examiner*—Bernard Helfin
*Assistant Examiner*—Nicky Chan
*Attorney, Agent, or Firm*—Corwin R. Horton; Stanley M. Teigland

[57] ABSTRACT

When 4,4'-dihydroxydiphenyl sulfone is sulfonated to form 3,3'-sulfonylbis(6-hydroxybenzene sulfonic acid), the product can be recovered from the reaction mixture by adding methanol or ethanol and a base to the reaction mixture to selectively precipitate only the disalt of the product. Particularly good results are obtained using sulfolane as a solvent in the sulfonation reaction. The product is useful as a flame retardant additive in polymers and other materials, and is also useful as an additive in boiler water to remove or prevent formation of scale.

3 Claims, No Drawings

METHOD OF PREPARING A DISALT OF 3,3-SULFONYLBIS (6-HYDROXYBENZENE SULFONIC ACID)

U.S. Pat. No. 2,171,806 and British Pat. No. 595,211 disclose that 4,4'-dihydroxydiphenyl sulfone can be sulfonated by reaction with a sulfonating agent to form 3,3'-sulfonylbis(6-hydroxybenzene sulfonic acid), which has the following structural formula

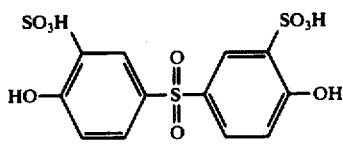

For convenience, this compound will be referred to as "disulfonated SDP." The letters "SDP" stand for sulfonyl diphenol, which is the name more commonly used in the art to refer to 4,4'- dihydroxydiphenyl sulfone.

In the referenced patents, the sulfonated SDP is not recovered from the reaction mixture, but is further reacted in situ to form other products. However, for certain applications it is necessary to recover the disulfonated SDP from the reaction mixture. This invention provides a convenient method for doing so.

In accordance with this invention, the disulfonated SDP is recovered from the reaction mixture by adding a base, which forms the corresponding disalt, and also adding methanol or ethanol, which selectively precipitates the disalt from the reaction mixture. Being the only solid present in the mixture, the disalt can be recovered therefrom in accordance with conventional methods, such as by filtration or centrifugation. By this process, the disalt is recovered in high yield at high purity. After the disalt is recovered, it can be reconverted to the diacid if desired in accordance with the conventional methods.

An important feature of this invention is that methanol and ethanol cause selective precipitation of only the disalt from the reaction mixture. The other components, including unreacted reactants, solvent (optional), by-products (e.g. water), monosulfonated SDP and its salt, disulfonated SDP and the monosalt of disulfonated SDP, all remain in solution. Methanol provides better selective precipitation than ethanol, and therefore is preferred. Of course, a mixture of methanol and ethanol can also be used.

In the sulfonation reaction, chlorosulfonic acid is preferred as the sulfonating agent in small operations; and sulfur trioxide, being less expensive and forming no by-product, is preferred for large scale operations. As disclosed in the prior art, excess chlorosulfonic acid may be used as the solvent in the reaction mixture, but in accordance with a preferred embodiment of this invention, sulfolane (tetrahydro thiophene-1,1-dioxide) is used as the solvent to facilitate recovery of the product in higher yield at higher purity. Sulfolane is a solvent for all components of the reaction mixture, including the alcohol, and all products.

When sulfolane is employed as a solvent, it is preferable to use a slight stoichiometric excess of the sulfonating agent in order to effect substantially complete disulfonation of the SDP.

The sulfonation reaction is usually carried out at a temperature in the range of 80° to 150° C, but higher or lower temperatures may be used if desired. The preferred range is 90° to 120° C. The pressure is not critical, but it is preferable to carry out the reaction under an inert atmosphere, such as nitrogen.

After the sulfonation reaction is carried out, a base and methanol and/or ethanol are added to precipitate the disalt of the disulfonated SDP. The base and the alcohol can be added in any order or simultaneously. However, it is preferable to add the alcohol first in order to form a more dilute solution and thereby insure against precipitation of other compounds.

The amount of alcohol added to the reaction mixture is that which converts the reaction medium from a solvent to a non-solvent for the disalt. The transition can be observed visually, so for any desired set of conditions, the amount of alcohol to be added can be determined by simple experimentation. In terms of operability, there is no upper limit to the amount of alcohol which can be added. For economical reasons, however, it is desirable to add only the minimum amount necessary to cause precipitation of the disalt. This amount depends primarily on the amount of solvent (e.g. sulfolane) present. As a general rule, from about 5 to about 20 parts by weight of alcohol are required for each part by weight of solvent. The exact amount required within the range depends on such factors as the concentration of the product and the temperature.

The higher the concentration of the product, the less alcohol is required for precipitation. Hence, to minimize the amount of solvent as well as the amount of alcohol employed in the process, the concentration of the product is preferably close to but below its saturation point in the reaction mixture upon completion of the sulfonation reaction.

If the concentration of the product is close to its saturation point, cooling of the mixture prior to the addition of alcohol will cause precipitation of the reaction product, which is permissible but not desirable. Hence, it is preferable to add the alcohol to the mixture as it is cooled. Cooling of the mixture reduces the solvating power of the solvents and thereby reduces the amount of alcohol required. However, it is not necessary to cool the mixture, and the alcohol can be added at any temperature.

An organic or inorganic base which is soluble in methanol or ethanol may be used to form the disalt. The base may be a hydroxide or the salt of a weak acid. The cation may be ammonium or any metal ion, but preferably is an alkali metal or alkaline earth metal ion. Alkali metal, particularly sodium and potassium, ions are preferred. The base is preferably a hydroxide because the only by-product it forms is water, which is more conveniently removed than the by-products formed by other bases. A slight stoichiometric excess of the base is preferably used to effect substantially complete neutralization of the disulfonated SDP. For convenience, the base may be added to the reaction mixture dissolved in the alcohol, but preferably only in the final portion of the alcohol added to the reaction mixture.

Water or a weak acid is generated as a by-product in the neutralization step; and water is also usually associated with the base as water of hydration. It is not necessary to remove the water or weak acid, but since they are also solvents for the disalt, if they are not removed, their solvating effect must be overcome by the addition of more alcohol. In other words, they, as well as any excess chlorosulfonic acid, should be considered as "solvent" is determining the amount of alcohol to be added to the mixture.

Disulfonated SDP and its salts are particularly useful as flame retardants. When exposed to a flame, the salts intumesce with the formation of voluminous black foam. They can be incorporated into polymers, either as additives or as part of the polymer structure, to improve flame resistance. The hydrogens of the hydroxyl groups can be replaced with other groups to form polymerizable derivatives in accordance with methods known in the art. The compounds can also be included in coatings, such as paints and varnishes. Being water-soluble, they can be incorporated into a water-absorbing material, such as wood, by treating it with an aqueous solution of the compound. The amount of the compound incorporated into a material to improve its flame resistance is preferably from about 5 to 20 percent by weight.

Disulfonated SDP and its salts are also useful as additives in water, such as boiler water, to remove or prevent formation of scale. A concentration of from about 0.005 to 4 percent by weight of the compound is preferred for this purpose. It is theorized that the sulfur-bonded oxygen atoms chelate metal ions. No metal ions are known which do not form water-soluble complexes with disulfonated SDP and its salts.

EXAMPLE 1

One mole of chlorosulfonic acid was slowly added to one-half mole of SDP with stirring. The mixture, which solidified after a short period of time, was heated overnight at 130° C and then dissolved in one liter of methanol. The resultant solution was poured into a solution of 100 grams of potassium acetate in one liter of methanol. The dipotassium salt of disulfonated SDP precipitated immediately and was recovered at a yield of 88%.

EXAMPLE 2

A reactor was charged with 1326.6 grams (5.45 moles) of SDP and 890 ml (1123 grams) of sulfolane. The contents were heated with stirring to 100° C as most, but not all, of the SDP dissolved. With the heat turned off, 1331 grams (11.42 moles) of chlorosulfonic acid were gradually added over a period of two hours. Due to the heat of the reaction, the temperature stayed between 100° and 108° C. The undissolved SDP dissolved within the first half hour of the addition. Heat was then applied to maintain the temperature at 100° C for 1.5 hours while nitrogen was bubbled through the stirred mixture to remove HCl. The mixture was stirred for another half hour without heat as the temperature dropped to 90° C and the solution became viscous. At this point 1.5 liters of methanol at ambient temperature were added to the solution over a period of half an hour. The contents of the reactor were then poured into 9.8 liters of methanol. A solution of 750 grams (86.5% assay) of potassium hydroxide (11.59 moles) in 2.2 liters of methanol was added over a period of half an hour, followed by the addition of 30 grams of acetic acid (buffer). A salt precipitated and was recovered by filtration to produce a 95 +% of the dipotassium salt of disulfonated SDP.

EXAMPLE 3

The end of a match stick was momentarily dipped into an aqueous solution of 20% by weight of the dipotassium salt of disulfonated SDP. The match was dried and dipped twice again before final drying. The match was then lit and proceeded to burn until the flame reached the salt, which intumesced and quickly extinguished the flame.

EXAMPLE 4

To prevent formation of scale, 40 grams of the dipotassium salt of disulfonated SDP are added to one liter of boiler water.

I claim:

1. A method of preparing an ammonium or alkali metal disalt of 3,3'-sulfonylbis (6-hydroxybenzene sulfonic acid) comprising
   a. reacting 4,4'-dihydroxyldiphenyl sulfone with a sulfonating agent selected from the group consisting of chlorosulfonic acid and sulfur trioxide in the presence of sulfolane as a solvent to form 3,3'-sulfonylbis(6-hydroxybenzene sulfonic acid),
   b. adding an alcohol selected from the group consisting of methanol and ethanol and a base soluble in the alcohol to the reaction mixture, the base being selected from the group consisting of hydroxides and salts of weak acids wherein the cation of the base is ammonium or an alkali metal, the base being present in an amount sufficient to form the disalt of 3,3'-sulfonylbis(6-hydroxybenzene sulfonic acid), and the alcohol being present in an amount sufficient to selectively precipitate the disalt, and
   c. recovering the disalt from the reaction mixture.

2. The method of claim 1 wherein the alcohol is methanol.

3. The method of claim 1 wherein the base is an alkali metal hydroxide.

* * * * *